United States Patent [19]

LaHaye et al.

[11] Patent Number: 4,719,825
[45] Date of Patent: Jan. 19, 1988

[54] METERING NEEDLE ASSEMBLY

[76] Inventors: Peter G. LaHaye, #3 Eucalyptus Ct., Woodside, Calif. 92062; Richard D. Phipps, 38450 Berkeley Common, Fremont, Calif. 94536; Robert L. Lathrop, 1667 Glenrock Ct., San Jose, Calif. 95124

[21] Appl. No.: 843,051

[22] Filed: Mar. 24, 1986

[51] Int. Cl.$^4$ ................................................. B43K 5/06
[52] U.S. Cl. ..................................... 81/9.22; 222/390; 128/316; 401/172; 604/155
[58] Field of Search .................. 81/9.22; 401/171, 172, 401/182, 66; 604/155, 208; 222/390, 391; 128/316

[56] References Cited

U.S. PATENT DOCUMENTS

| 3,790,048 | 2/1974 | Luciano et al. | 222/391 X |
| 4,103,370 | 3/1977 | Gingras | 222/390 X |
| 4,204,438 | 5/1980 | Binaris et al. | |
| 4,585,439 | 4/1986 | Michel | 604/155 |

OTHER PUBLICATIONS

The Permanent Camouflage of Port-Wine Stain of the Face by Intradermal Injection of Insoluable Pigments (Tattooing) presented at the 142nd Annual Meeting of the Medical Society of the State of New York, New York City, Section on Dermatology and Syphilology (4 pages), May 21, 1948.
Spaulding & Rogers—Tattoo Supplies (5 pages).

Primary Examiner—Debra Meislin
Attorney, Agent, or Firm—Price, Gess & Ubell

[57] ABSTRACT

A tattooing device includes a disposable syringe in which a tattoo dye is dispensed through a passageway in a needle of the syringe. A cam member is rotated to rotate a clutch rod held in a clutch member. The clutch rod rotates a threaded rod through a fixed nut member that causes the threaded rod to move linearly towards the syringe to displace a plunger pin fixed to the threaded rod. The plunger pin thereby displaces a plunger of the syringe to dispense the tattoo dye through the needle.

11 Claims, 7 Drawing Figures

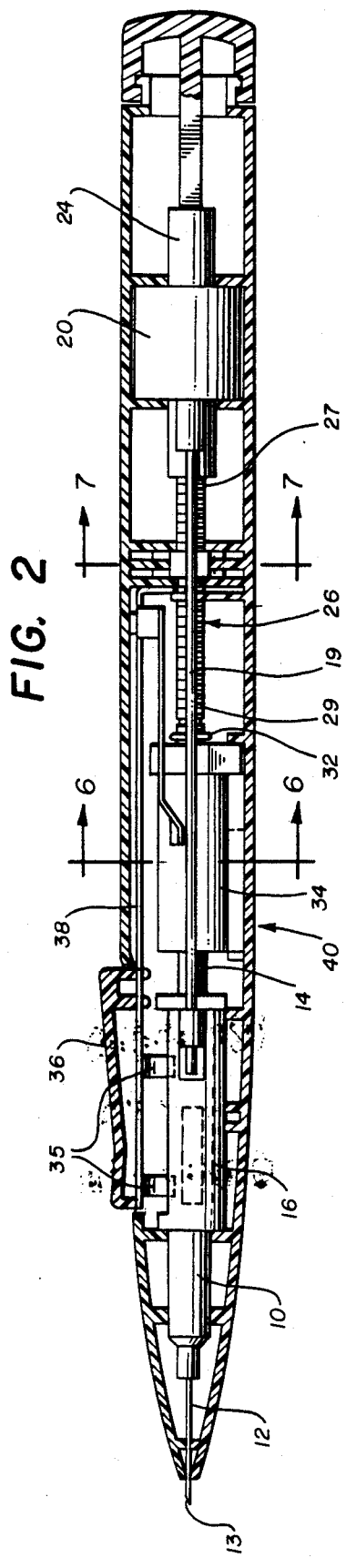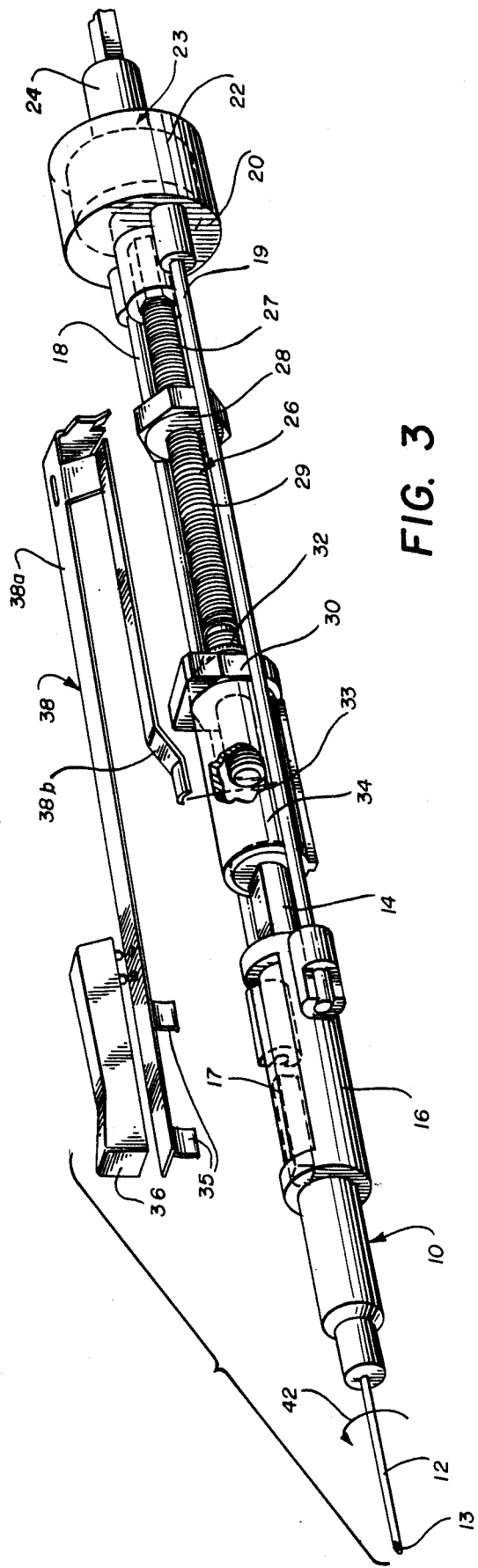

METERING NEEDLE ASSEMBLY

BACKGROUND OF THE INVENTION

1. Field of the Invention

The present invention generally relates to dispensing devices for injecting fluid and, more specifically, to an improved tattooing device that repeatedly dispenses liquid pigment material in predetermined measured amounts.

2. Brief Description of the Prior Art

Devices to tattoo various parts of the human body have long been used. Pictorial designs and identification marks have been commonly tattooed onto human and animal skin. Generally, an electric motor or solenoid is used to reciprocate a needle having a liquid dye coated on its external surface. The reciprocating needle is then inserted into the skin. For example, the Binaris et al, "Tattooing Device," U.S. Pat. No. 4,204,438 discloses a bulky motor housing attached to a needle housing for performing tattooing. A motor within the motor housing is powered by batteries for reciprocation of a tattooing needle. The tattoo needle is dipped into a tattoo dye and the device is activated by particular angular positions of the device as it is held in a user's hand.

One shortcoming in the prior art is that the devices have been generally bulky in shape, heavy in weight, and usually vibrate. In addition, having to dip the needle into a container of dye does not permit the use of dye in a measured amount nor the repeated use of the dye in the same measured amounts.

The medical profession has recently used pneumatic and electrically driven handheld devices, that are relatively lightweight compared to commercial tattoo units, for cosmetic tattooing. Further, the use of a solenoid to rapidly reciprocate the needle has a propensity to tear the skin being tattooed, impairs hair follicle growth, and makes detailed work difficult. The problems in the prior art become more obvious when greater detail and precision is required in the tattooing work, such as in cosmetic tattooing around the human eye. Additionally, the tattoo dye is splattered about the situs of the implant and obscures the placement of additional implants of dye.

Medical syringes with the ability to meter fixed quantities of inexpensive dye are also known in the prior art.

There is still a demand in the medical industry to provide an improved inexpensive metering needle assembly that can be used for cosmetic tattooing and the like.

SUMMARY OF THE INVENTION

One object of the present invention is to provide an improved tattooing device configured to be held freely in a person's hand like a writing instrument, and capable of being mechanically activated by the use of a finger of the hand holding the device.

Another object of the present invention is to provide a device which is lightweight and thereby allows ease of use particularly when the area being worked on is small or the substance being worked on is delicate.

In addition, an object of the present invention is to do away with the need to reciprocate a tattoo needle and instead dispense the tattoo dye directly through a passageway through a tip of a nonreciprocating needle.

A further object is to dispense the tattoo dye in predetermined measured amounts.

The preferred embodiment of the present invention accomlishes these objects by providing, among other things, a self contained housing which is configured to resemble a writing pen. A disposable syringe, which contains a tattooing dye cartridge, is held within one end of the housing. An activator near the syringe can be mechanically activated by a finger of the hand holding the device. The activator rotates a cam member and a clutch member which, in turn, rotate a threaded rod which moves within the housing to displace a plunger in the syringe to dispense measured amounts of the tattooing dye.

These and other objects of the present invention will be evident from examining the drawings, specification and claims attached hereto.

BRIEF DESCRIPTION OF THE DRAWINGS

FIG. 2 is an enlarged sectional view taken about line 2—2 in FIG. 1;

FIG. 3 is an enlarged perspective view of FIG. 1 with the outer casing removed to illustrate the interior elements thereof;

DETAILED DESCRIPTION OF THE PREFERRED EMBODIMENT

The following description is provided to enable any person skilled in the tattooing and medical cosmetic fields to make and use the present invention and sets forth the best modes contemplated by the inventors of carrying out their invention. Various modifications, however, will remain readily apparent to those skilled in the art, since the generic principles of the present invention have been defined herein specifically to provide an improved metering needle assembly.

Figure 1:
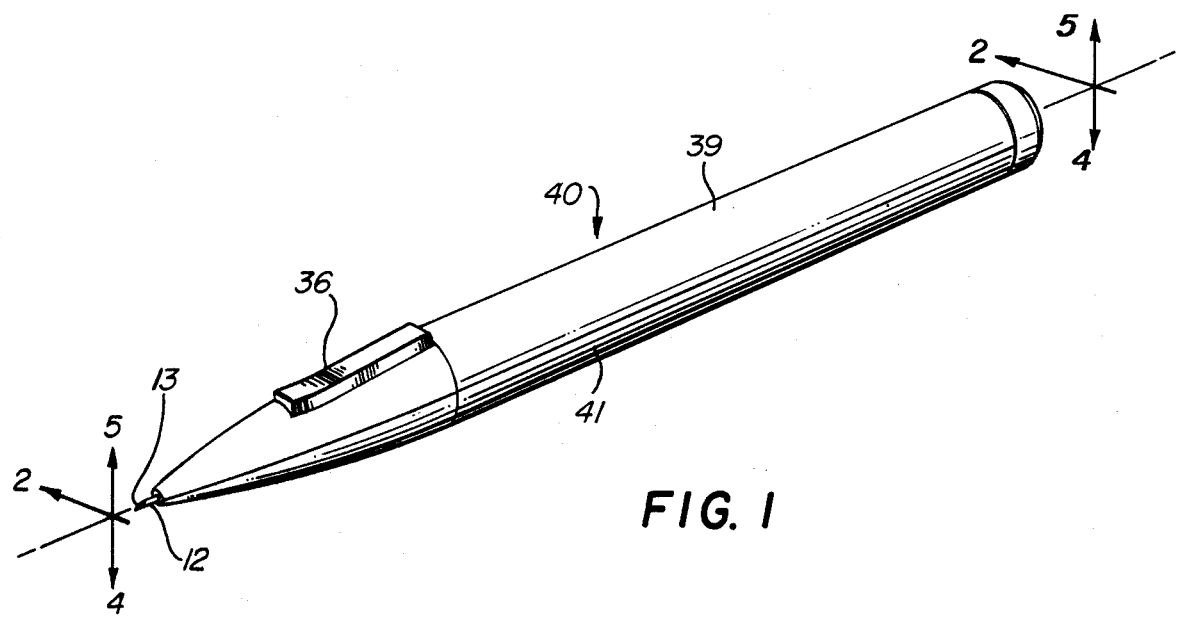
FIG. 1 is a perspective view of a preferred embodiment of the present invention.

Referring to FIG. 1, a housing 40 supports the various operative elements of the invention and is preferably an elongated, tube-shaped element positioned along a longitudinal axis having a top portion 39 and a bottom portion 41, both of which form a front tapered end of the housing 40 and are separable from each other for access to other elements of the invention as described below. The top portion 39 and the bottom portion 40 are held together during operation of the preferred embodiment by conventional frictional engagement of the edges thereof, or by using a third element wrapped about both portions, or other suitable means conventional in the art. The configuration of the housing 40 resembles a writting pen but can be varied within the parameters of the invention and is perferably formed of a medical grade plastic.

A replaceable syringe assembly 10 is held in a recess in the front tapered end of the housing 40 and has at one end a cylindrical cavity positioned on the longitudinal axis, a plunger 14 disposed in the cylindrical cavity, and a needle 12 at the other end.

The needle 12 is hollow and provides a passageway 13 along the longitudinal axis and is of such a length to extend out of the tapered end of the housing 40 to permit piercing of the skin. The syringe assembly 10, needle 12 and plunger 14 are of conventional designs and are disposable to permit sterile replacements to be added. The plunger 14 moves along the longitudinal axis within the syringe assembly 10 to dispense a predetermined portion of a tattoo dye reservoir 11 (FIG. 4) contained in the cylindrical cavity through the passageway 13 when the needle 12 is inserted into the skin. Following the dispensing of all the tattoo dye in the reservoir 11, the syringe assembly 10 is removable from the housing 40 upon separating the top portion 39 from the bottom portion 41 to allow the sterile replacement of another syringe assembly 10 filled with tattoo dye.

Figure 4:
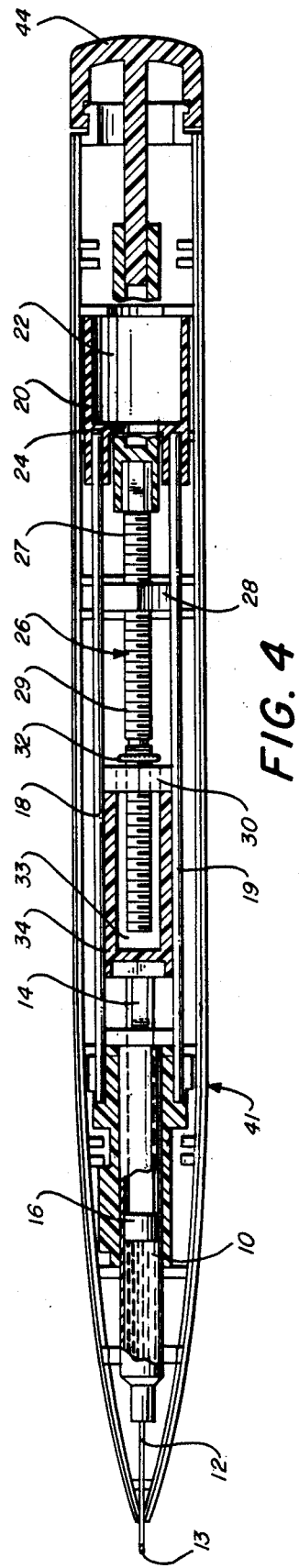
FIG. 4 is an enlarged sectional view taken about line 4—4 of FIG. 1.
Figure 5:
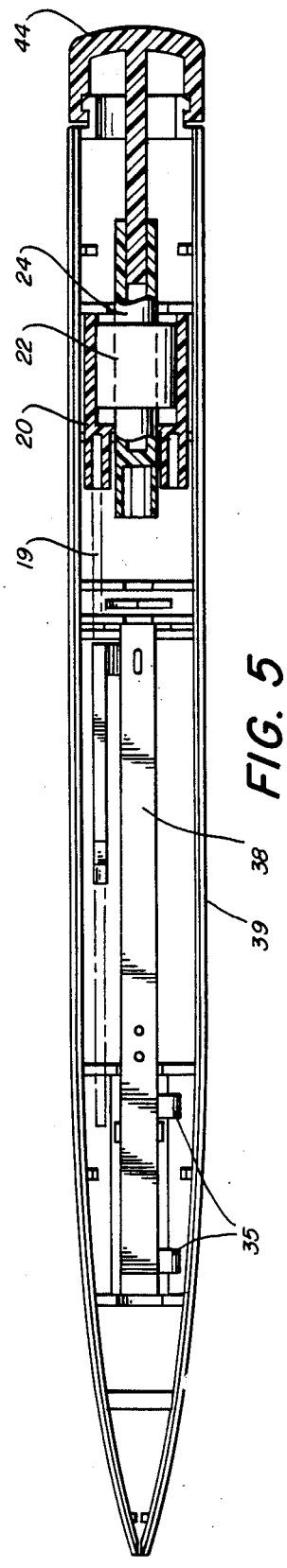
FIG. 5 is an enlarged sectional view taken about line 5—5 of FIG. 1.

A cam member 16 is rotatably disposed about the cylindrical cavity portion of the syringe assembly 10. The cam member 16 is a tube-shaped element whose longitudinal axis lies along the longitudinal axis of the housing 40, as best shown in FIGS. 2, 3, and 4. A pair of projections 17 are disposed on the exterior surface of the cam member 16 at one side thereof that is adjacent the engaged edges of the top portion 39 and the bottom portion 41. The portion of the exterior surface of the cam member 16 opposite the top portion 39 defines a rectangular shaped aperture and exposes a part of the cylindrical cavity portion of the syringe assembly 10. In FIG. 4, a pair of pins or elongated rods 18, 19 of a metal, spring-like material are fixedly connected on the external surface of the cam member 16 and extend torwards the end of the housing 40 opposite its tapered end. The pins 18, 19 are positioned parallel to the longitudinal axis on opposite sides thereof. The pin 18 is fixed to the cam member 16 on the side upon which the projections 17 are located, while the pin 19 is fixed on the opposite side thereof.

A spring assembly 38 includes a first leaf spring 38a and a second leaf spring 38b. One end of both the first leaf spring 38a and the second leaf spring 38b are joined together in a generally "U"-shaped configuration, and is fixed to the top portion 39 of the housing near its middle part along the longitudinal axis and serves as a point about which each spring is cantilevered. Both the first leaf spring 38a and the second leaf spring 38b are thin, elongated, rectangular shaped metallic elements which extend from the fixed point at which they are cantilevered towards the syringe assembly 10. The first leaf spring 38a is longer in length than the second leaf spring 38b and extends over the rectangular shaped aperture of the cam member 16 and has at such end a pair of apertures and a pair of projections 35 that extend down towards the cam member 16 to frictionally engage the corresponding pair of projections 17 upon activation of a button 36, as described below. The second leaf spring 38b extends above the pin 19 to permit the end thereof to contact the pin 19 as the pin 19 rotates with the cam member 16 in the manner described below.

The button or activator 36 is a rectangular shaped element disposed in a similarly shaped aperture in the tapered end of the top portion 39. The button 36 includes a pair of rounded projections on its external surface facing the bottom portion 41 and fit in the two apertures at the end of the first leaf spring 38b, as shown in FIG. 3. Upon activation by a finger of a user's hand, the button 36 moves in a plane generally perpendicular to the longitudinal axis of the housing 40.

The ends of the pins 18, 19 which are opposite to those fixed to the cam member 16 are fixed to opposing lateral sides of the exterior surface of a sleeve 20. Pins 18, 19 fix the position of the sleeve 20 both rotationally about the longitudinal axis and linearly along the longitudinal axis with respect to the cam member 16, as will be further described below. The sleeve 20 is a cylindrical shaped plastic element having a bore positioned on the longitudinal axis and whose circular cross section is larger than the circular cross section of the cam member 16.

A clutch member 22 is fixed inside the bore of the sleeve 20 and defines an aperture 23 which is a cylindrical shaped bore whose longitudinal axis lies along the longitudinal axis of the housing 40. In the preferred embodiment, the clutch member 22 is of a conventional design manufactured by Torrington, a division of Ingersol-Rand, model no. RC-040708, and is designed with bearings (not shown) that hold an element in the aperture 23 while allowing the element to slide along the longitudinal axis, and rotate about the longitudinal axis in one direction only, which, in this embodiment, is in a clockwise direction 42. The clutch member 22 is fixed in the sleeve 20 by an adhesive element or any other suitable conventional means so that the clutch member 22 rotates with the rotation of the sleeve 20 which is caused by the rotation of the cam member 16, as described below.

A clutch rod 24 is journalled in the aperture 23 of the clutch member 22 and is thereby permitted to rotate therein in the clockwise direction 42 and to slide along the longitudinal axis. The purpose of the clutch rod 24 is to transfer rotational movement of the clutch member 22 to a threaded rod 26 described below. The clutch rod 24 is an elongated, rod-shaped metallic element having a circular cross section slightly smaller than the circular cross section of the aperture 23 and is of a length longer than the axial length of the clutch member 22. The end of the clutch rod 24, disposed farthest from the cam member 16, defines a rectangular shaped bore that extends along the axial length of the clutch rod 24. Such a rectangular shaped bore serves to slidably hold an elongated, rectangular shaped post member of an end cap 44 that extends out of the housing 40 at the end opposite the tapered end. The end cap 44 has a cylindrical shaped portion outside of the housing 40 which is dimensioned so that its circular cross section is approximately equal to the circular cross section of the end of the housing 40 which the end cap 44 encloses. The end cap 44 further includes an inwardly flanged edge that frictionally engages an outwardly flanged edge of the housing 40 to thereby permit the end cap 44 to rotate about the longitudinal axis of the housing 40, but not move linearly along the longitudinal axis.

The end of the clutch rod 24 which is disposed nearest the cam member 16 is connected to one end of a threaded rod 26 which lies along the longitudinal axis so that the threaded rod 26 rotates with any rotation of the rod clutch 24 which is imparted by the clutch member 22. The threaded rod 26 provides a transmission of a set displacement from the button 36 to the plunger 14. The threaded rod 26 is of a length that is longer than the clutch rod 24 but shorter than the pins 18, 19. The external surface of the threaded rod 26 has a first helical thread 27 disposed over approximately half of it while a second helical thread 29 covers the other half. The first thread 27 is disposed on a half of the threaded rod 26 near the connection of the threaded rod 26 with the clutch rod 24. The second thread 29 has a pitch size smaller than the first thread 27. In the preferred embodiment, the first thread 27 is of a standard #6-32 size and the second thread 29 is of a standard #6-40 size. However, as will be evident from the following specifications, other sizes of threads are contemplated.

Figure 6:
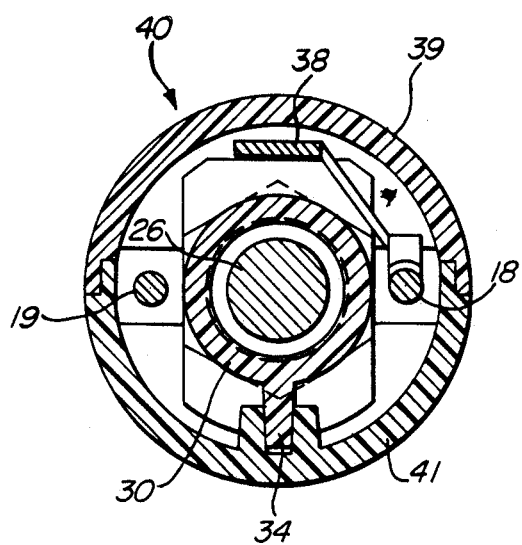
FIG. 6 is an enlarged cross-sectional view taken about line 6—6 of FIG. 2.
Figure 7:
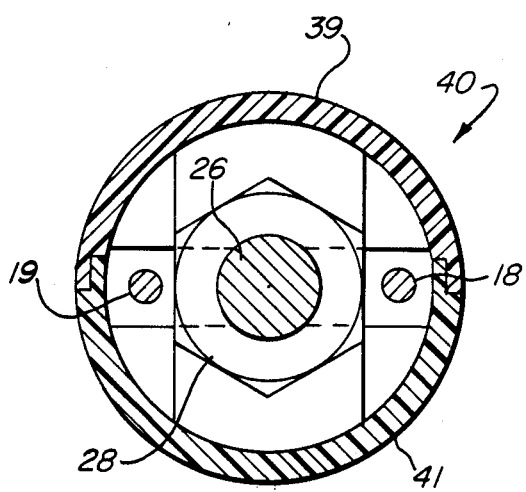
FIG. 7 is an enlarged cross-sectional view taken about line 7—7 of FIG. 2.

Referring to FIGS. 2, 3, and 7, threaded onto the first thread 27 is a nut member 27 which sits in a recess of the housing 40 and is thus fixed relative to the housing 40. The nut member 28 has a helical grooves of a size to receive the first thread 27. A plunger pin 34 is positioned along the longitudinal axis adjacent the plunger 14 and is a generally elongated, cylindrical shaped plastic element defining an aperture 33 along its entire longitudinal axis and has a circular cross section larger than the circular cross section of the threaded rod 26. The plunger pin 34 is threadably mounted onto the second thread 29 by a retainer nut 30 disposed in that end of the plunger pin 34 opposite the plunger 14, as shown in FIG. 6. The threaded rod 26 is thereby permitted to rotate within the retainer nut 30 and into the aperture 33 of the plunger pin 34. The external surface of the end of the plunger pin 34 which is opposite the retainer nut 30 and adjacent the plunger 14 is recessed to receive the end of the plunger 14. Further, the external surface of the plunger pin 34 opposite the bottom portion 41 is configured to include a raised rectangular shaped area that slidably sits in a recess of the bottom portion 41 so that the plunger pin 34 is restrained from rotation in the housing 40 but is permitted to be linearly displaced along the longitudinal axis. An O-ring 32, preferably of rubber, is disposed on the threaded rod 26 and abuts the retainer nut 30 while intermediate the retainer nut 30 and the nut 28 member. The O-ring 32 has an interior circumference slightly larger than the exterior circumference of the threaded rod 26 and minimizes reverse rotation of the rod 26 in the nut 30.

Having described the elements in the preferred embodiment of the present invention, the following describes the manner of operation of the elements in the preferred embodiment. The user first snaps the end cap 44 off the housing 40 and slides the end cap 44 out of the clutch rod 24, separates the top portion 39 from the bottom portion 41, then removes the various operational elements described above. The syringe assembly 10 which contains a tattoo dye is then placed in the bottom portion 41 at the tapered end thereof. The nut member 28 is rotated about the first threads 27 of the threaded rod 26 to a position near the middle of the threaded rod 26. The retainer nut 30 attached in the plunger pin 34 is then rotated on the threaded rod 26 to a position near the end of the second thread 29 farthest from the first thread 27. The cam member 16 is then slid over the cavity portion of the syringe assembly 10, the plunger pin 34 is positioned in its respective recess in the bottom portion 41, and the nut member 28 is adjusted in its respective recess in the bottom portion 41. The top portion 39 is then engaged to the bottom portion 41, and the post member of the end cap 44 is inserted into the bore of the clutch rod 24. The end cap 44 is then rotated in the clockwise direction 42 until the tattoo dye from the reservoir 11 just begins to be dispensed out of the passageway 13 of the needle 12.

The user can then insert the needle 12 into the skin. Upon depression of the button 36 into the housing 40, the projections 35 of the first leaf spring 38a frictionally engage the projections 17 of the cam member 16. The cam member 16 thereby initially rotates in the clockwise direction 42 about the longitudinal axis. Upon rotation of the cam member 16, the pins 18, 19 similarily rotate. The end of the second leaf spring 38b then contacts the pin 19 and provides a spring action to bias the rotation of the cam member 16. Because the clutch member 22 is stationarily fixed within the sleeve 20, which is stationarily fixed to the cam member 16 by the pins 18, 19, the rotation of the cam member 16 causes the clutch member 22 to rotate in the clockwise direction 42. Likewise, because the clutch rod 24 is held within the aperture 23 of the clutch member 22, the clutch rod 24 also rotates in the clockwise direction 42 together with the end cap 44.

The rotation of the clutch rod 24 is transmitted to the threaded rod 26 whose first thread 27 then rotates through the nut member 28. Thereby, the threaded rod 26 moves linearly along the longitudinal axis and consequently pulls the clutch rod 24 through the aperture 23 of the clutch member 22 along the longitudinal axis and away from the post member of the end cap 44. At the same time, the second thread 29 rotates through the O-ring 32 and the retainer nut 30 and thereby linearly displaces the plunger pin 34 toward the plunger 14. Because of the difference in thread pitch between the first thread 27 and second thread 29, the effective linear displacement of the plunger pin 34 is reduced below that which would otherwise occur with only the first thread 27 disposed over the entire surface of teh threaded rod 26 to provide a gear reduction in the transmission of the motion. Further, the displacement of the plunger pin 34 is of a predetermined amount which is determined by the pitches of the first thread 27, the second thread 29 and the amount by which the threaded rod 26 is rotated. Being radially fixed to the housing 40, the plunger pin 34 moves linearly in a predetermined amount towards the plunger 14. The plunger 14 thus advances through the cavity of the syringer assembly 10 towards the needle 12 in the same amount of movement as the plunger pin 34. As a result, a predetermined amount of dye is dispensed through the passageway 13 of the needle 12 since the volume displaced is a cylindrical volume, linearly proportionate to the axial movement.

As briefly described above, as the button 36 is depressed into the housing 40, the second leaf spring 38b begins to bias the pin 19 and thereby rotates the cam member 16, the sleeve 20, and clutch member 22 in the counterclockwise direction. The button 36 becomes fully depressed when the end of the first leaf spring 38a, upon which the button 36 is mounted, moves into the aperture on the top portion of the cam member 16 and rests on the cavity portion of the syringe assembly 10. At such time, the cam member 16 is no longer rotated and thus the tattoo dye is no longer dispensed. When the button 36 is released, the second leaf spring 38b rotates the pin 19 in the counterclockwise direction to return the pin 19 to its position prior to rotation in clockwise direction 12 and to restore the button 36 to its initial position. Consequently, the cam member 16, the sleeve 20, and the clutch member 22 are returned to their initial positions prior to rotation in the clockwise direction 12 However, the clutch rod 24 remains stationary while the clutch member 22 returns to its initial position, since the clutch member 22 holds the clutch rod 24 while rotating in the clockwise direction 12 and releases it in the counterclockwise direction. As a result, and with the assistance of the frictional forces that the O-ring 32 imparts to the threaded rod 26 and the retainer nut 30, the threaded rod 26 and the plunger pin 34 do not return to their initial positions prior to the clockwise rotation of the cam member 16, the sleeve 20, and the clutch member 22, but remain stationary.

As can be seen, repeated depressions of the button 36 results in the plunger 14 being repeatedly displaced along the longitudinal axis in the predetermined amounts described above. In so doing, the tattoo dye in the syringe assembly 10 is dispensed through the passageway 13 of the needle 12 in precise, predetermined measured amounts. This manner of operation allows a user to insert the needle 12 into a precise location of the skin and then to depress the button 36 to inject a predetermined amount of tattoo dye at such location. If additional tattoo dye is desired at the location, the button 36 is depressed an appropriate number of times. The needle 12 is then removed from such location and inserted into the skin at the next desired location. This procedure can be repeated until the tattoo dye in the syringe asembly 10 is completely dispensed. If further tattooing is needed, a sterile replacement of a syringe assembly 10 filled with tattoo dye can be made.

Further, as can be seen, if the button 36 is only partially depressed into the housing 40, it is evident that the amount of tattoo dye dispensed will be less than the maximum predetermined measured amount. However, the present invention contemplates that not more than the predetermined measured amount can be dispensed upon a full cyclic depression of the button 36. Also, while the preferred embodiment describes the first thread 27 as having a standard pitch size #6-32 and the second thread 29 as having a standard pitch size #6-40, the present invention also contemplates that such pitch dimesnions can be appropriately changed to alter the incremental displacement of the plunger 14 along the longitudinal axis. In addition, the material and configuration of the spring assembly 38 and the amount by which the button 36 can thereby rotate the cam member 16 can be altered to change the rotational dis- placement of the cam member 16 in the clockwise direction 42 which will in turn alter the incremental displacement of the plunger 14.

It should be understood, of course, that the foregoing relates to a preferred embodiment of the invention and that modifications may be made without departing from the sprit and scope of the invention as set forth in the following claims.

We claim:

1. A tattooing device, comprising:
 a needle having a passageway therein;
 means for holding a liquid in communication with the passageway, said holding means includes a plunger having a first end and a second end;
 means for dispensing a selected portion of the liquid, said dispensing means includes:
  a plunger pin having a first end attached to a stationary nut member for engagement with a threaded rod, a second end of said pin being in engagement with said second end of said pin being in engagement with said second end of said plunger, wherein rotational movement of the threaded rod is converted to linear displacement of said plunger along the longitudinal axis;
  a clutch member connected to the threaded rod to rotate the threaded rod about a longitudinal axis upon activation of the clutch member;
  a cam member operatively fixed to the clutch member to permit activation of the clutch member; and
  a spring means adjacent the cam member to provide rotational movement to the cam member.

2. The invention of claim 1 wherein the spring means includes a first leaf spring and a second leaf spring to limit the amount by which the cam member can be rotated.

3. The invention of claim 2 wherein one of the first leaf spring and the second leaf spring rotates the cam member in a first direction about the longitudinal axis and the other of the first leaf spring and the second leaf spring rotates the cam member in a second direction opposite the first direction.

4. The invention of claim 1 further comprising a button fixed to the spring assembly to assist in biasing the spring assembly upon depression by a user and thereby repeatedly rotating the cam member.

5. The invention of claim 1 further comprising means for supporting the needle, the holding means and the dispensing means, all of which are of a weight and configuration to enable them to be held like a writing instrument in a person's hand.

6. A tattooing device, comprising:
 means for holding a liquid, said holding means includes:
  a housing having a cavity portion, a plunger in the cavity portion, and a needle having a passageway therein attached to said housing;
  a threaded rod having a first end in threadable engagement with a nut member, said nut member being attached to one end of a plunger pin, a second end of said plunger pin being in engagement with said plunger, wherein rotational movement of the threaded rod is converted to linear displacement along a longitudinal axis to thereby move the plunger along said axis to dispense a selected portion of the liquid;
  a clutch member connected to a second end of the threaded rod to transfer rotation of the threaded rod upon rotation of the clutch member;
  a cam member disposed about the housing and fixed to the clutch member to provide rotational movement to the clutch member;
 first means for longitudinally and rotationally connecting the clutch member to the cam member;
 second means for connecting the clutch member to the threaded rod;
 a spring assembly having a first leaf spring adjacent the first connecting means and a second leaf spring adjacent the cam member for intermittent engagement therewith; and
 housing means supporting the threaded rod, the clutch member, the cam member, and the spring assembly.

7. The invention of claim 6 wherein the first connecting means comprises:
 a plurality of pins each having a first end and a second end, the first ends being fixed to the cam member; and
 a sleeve that holds the clutch member and is fixed to each of the second ends of the pins.

8. The invention of claim 6 wherein the clutch member defines an aperture with a bearing assembly therein that allows a clutch rod element to rotate therein about the longitudinal axis in one direction only, and slide therein along the longitudinal axis.

9. The invention of claim 8 wherein the second connecting means comprises a clutch rod held in the aperture of the clutch member and fixed to the threaded rod.

10. The invention of claim 9 wherein the plunger pin is radially fixed to the supporting means to prevent rotation with the threaded rod but allow linear displacement.

11. The invention of claim 9 wherein the threaded rod has helical threads on its external surface, the threads having two different pitches, the smaller pitch being on the portion of the threaded rod to which the plunger pin is fixed.

* * * * *